United States Patent
Van der Hulst

(10) Patent No.: US 9,333,282 B2
(45) Date of Patent: May 10, 2016

(54) WOUND-STIMULATING UNIT AND METHOD

(75) Inventor: Rene Remmelt Willie Johan Van der Hulst, Maastricht (NL)

(73) Assignee: KCI Medical Resources, Grand Cayman (KY)

( * ) Notice: Subject to any disclaimer, the term of this patent is extended or adjusted under 35 U.S.C. 154(b) by 2182 days.

(21) Appl. No.: 11/468,700

(22) Filed: Aug. 30, 2006

(65) Prior Publication Data

US 2008/0033325 A1    Feb. 7, 2008

(51) Int. Cl.
*A61M 1/00* (2006.01)

(52) U.S. Cl.
CPC ........... *A61M 1/0084* (2013.01); *A61M 1/0088* (2013.01)

(58) Field of Classification Search
USPC ........ 601/6–11; 604/313–317, 543, 304–305, 604/310–311, 307, 540; 424/422–426; 602/2, 48
See application file for complete search history.

(56) References Cited

U.S. PATENT DOCUMENTS

| | | | | |
|---|---|---|---|---|
| 3,964,482 | A | 6/1976 | Gerstel et al. | 604/890.1 |
| 6,626,891 | B2 * | 9/2003 | Ohmstede | 604/543 |
| 6,743,211 | B1 * | 6/2004 | Prausnitz et al. | 604/239 |
| 7,144,390 | B1 * | 12/2006 | Hannigan et al. | 604/313 |
| 7,520,872 | B2 * | 4/2009 | Biggie et al. | 604/319 |
| 2002/0065494 | A1 | 5/2002 | Lockwood et al. | 604/313 |
| 2003/0108587 | A1 * | 6/2003 | Orgill et al. | 424/423 |
| 2003/0187423 | A1 | 10/2003 | Wilkinson et al. | 604/506 |
| 2003/0216672 | A1 * | 11/2003 | Rastegar et al. | 601/9 |
| 2006/0155260 | A1 * | 7/2006 | Blott et al. | 604/543 |

FOREIGN PATENT DOCUMENTS

| | | |
|---|---|---|
| WO | WO 00/59424 | 10/2000 |
| WO | WO 01/93946 | 12/2001 |
| WO | WO 02/05890 | 1/2002 |
| WO | WO 02/083046 | 10/2002 |
| WO | WO 03/049610 | 6/2003 |
| WO | WO 2007/019038 | 2/2007 |

OTHER PUBLICATIONS

Novelty Search conducted by the Danish Patent and Trademark Office, dated Sep. 18, 2008.

* cited by examiner

*Primary Examiner* — Rachel Young

(57) ABSTRACT

The invention relates to a wound-stimulating unit comprising a wound-stimulating device for use in combination with a vacuum assisted closure. The closure comprises a hydrophilic body to be placed on a wound surface, a cover sealing the hydrophilic body and a skin portion surrounding the wound surface, and a vacuum system for generating an underpressure in a closure space limited by the wound surface, the skin portion surrounding the wound surface and the cover. Further, the wound-stimulating device comprises a connector provided with an intermediate channel structure having an input section and multiple output sections, the device further comprising a pressure system for supplying wound stimulating agents to the input section of the intermediate channel structure.

10 Claims, 1 Drawing Sheet

WOUND-STIMULATING UNIT AND METHOD

RELATED APPLICATIONS

This application claims benefit of European Application Serial Number 06076528.6 entitled 'Wound-Stimulating Unit and Method' filed on Aug. 4, 2006, which application is incorporated herein in its entirety by reference.

TECHNICAL FIELD

The invention relates to a wound-stimulating unit.

BACKGROUND OF THE INVENTION

Chronic wounds have a complicated pathophysiology. Usually, intervention in wound healing is focused on different aspects of this pathophysiology. During use of known bandages in treating chronic wound interaction occurs with respect to different aspects, such as modulating metalloproteinase, optimizing moisture and controlling of infection.

However, no evidence has been found indicating that such interventions have much effect. This might be due to the fact that such interventions are focused on merely one or a few pathophysiological aspects of chronic wounds.

A vacuum assisted closure (VAC) that is known from e.g. International patent publication WO 00/59424 interferes with multiple pathophysiological aspects of chronic wounds. A VAC comprises a hydrophilic body to be placed on a wound surface for receiving drained moisture of the wound, a cover sealing the hydrophilic body and a skin portion surrounding the wound surface, and a vacuum system for generating an underpressure in a closure space limited by the wound surface, the skin portion surrounding the wound surface and the cover.

It has been found that wound-stimulating agents, such as nutrition, growing stimulating materials and/or medicines, e.g. antibiotics, may have a beneficial effect during wound healing. As a disadvantage, it has also been found that it is very difficult to supply wound-stimulating agents to the wound, as inserted agents are immediately sucked away due to the underpressure in the closure space.

The present invention is directed toward overcoming one or more of the problems discussed above.

BRIEF DESCRIPTION OF THE DRAWINGS

By way of example only, embodiments of the present invention will now be described with reference to the accompanying figures in which.

The figures are merely schematic views of a preferred embodiment according to the invention. In the figures, the same reference numbers refer to equal or corresponding parts.

SUMMARY OF THE INVENTION

Figure 1:
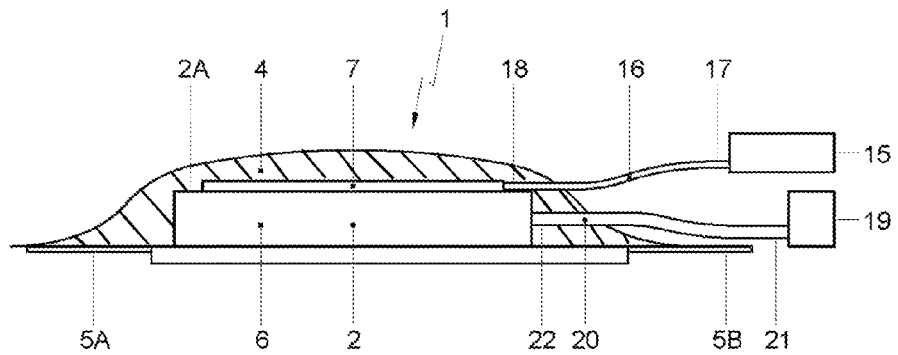
FIG. 1 shows a schematic view of a cross section of a wound-stimulating unit according to the invention in an atmospheric state.

It is an object of the invention to provide a woudstimulating unit, wherein the disadvantage identified above is reduced. In particular, the invention aims at obtaining a wound-stimulating unit wherein wound-stimulating agents can be supplied in a vacuum assisted closure that are not immediately sucked away. Thereto, according to an aspect of the invention, the wound-stimulating unit comprises a wound-stimulating device for use in combination with a vacuum assisted closure, wherein the wound-stimulating device comprises a connector provided with an intermediate channel structure having an input section and multiple output sections, the device further comprising a pressure system for supplying wound stimulating agents to the input section of the intermediate channel structure.

By applying a wound-stimulating device in combination with a vacuum assisted closure, the proven advantages of the vacuum assisted closure can be combined the feature of successful supplying wound-stimulating agents. By further providing a pressure system for supplying wound stimulating agents to the input section of the intermediate channel structure, wound-stimulating agents can be supplied under pressure into the vacuum assisted closure. In addition, by providing a connector that has an intermediate channel structure with an input section and multiple output sections the supplied stimulating agents can be distributed and directed to the wound surface or even to the wound tissue under the wound surface, so that the stimulating agents are not directly sucked away by the underpressure system.

In a very attractive embodiment according to the invention, the wound-stimulating unit comprises multiple microtubes each having a connector end being connected to an output section of the intermediate channel structure, so that the wound-stimulating agents can advantageously be directed and/or brought to desired locations near or inside the wound tissue. As an alternative, the wound-stimulating agents are injected by the output sections of the intermediate channel structure, so that a cheaper system is obtained which might be used if the generated pressure in the intermediate channel structure is high enough to enforce that the wound-stimulating agents reach their desired location.

Advantageously, the intermediate channel structure substantially extends in a connector plane that is during use substantially along the wound surface, wherein the multiple microtubes are substantially oriented transverse with respect to the connector plane, so that the wound stimulating agents can easily be brought near or into the wound tissue. Further the chance that the connection between the microtubes and the intermediate channel structure remains intact thus improves during the application of an underpressure, as shear forces on the connector ends of the microtubes are relatively small or absent.

In a preferred embodiment, the hydrophilic body is squeezable and the microtubes each have a protruding end extending away from the connector and penetrating the hydrophilic body such that in an atmospheric state of the vacuum assisted closure the protruding ends of the microtubes extend to near the wound surface and that in an underpressure state of the vacuum assisted closure the microtubes penetrate through the wound surface into wound tissue. In this way, the protruding ends of the microtubes can be positioned above the surface skin during attaching the wound-stimulating unit to the wound while in an elegant way the generation of the underpressure in the closure space also causes the protruding ends of the microtubes to penetrate the wound surface so that wound-stimulating agents can directly be supplied to wound tissue below the wound surface. The movement of the protruding ends of the microtubes is driven by an orientation of the protruding ends towards the wound surface and by the fact that by using a squeezable hydrophilic body the volume in the closure space is reduced during the generation of local underpressure. It is stated however, that the protruding ends can also be brought, during transferral of the atmospheric state to the underpressure state in a position near and above the wound surface, e.g. if (further) damage of the wound surface is to be avoided.

By providing a control unit to the pressure system, wherein the control unit is arranged for supplying wound stimulating agents to the input section of the intermediate channel structure in a continuous or intermitted way, the start, end, volume and way of the stimulating agents supply can advantageously be controlled. Alternatively, the pressure system does not comprise an explicit control unit, but provides a static pressure that can manually be activated and terminated The invention further relates to a method.

Other advantageous embodiments according to the invention are described in the following claims.

DETAILED DESCRIPTION OF THE INVENTION

FIG. 1 shows a schematic view of a cross section of a wound-stimulating unit 1 according to the invention in an atmospheric state. The wound-stimulating unit 1 that consists of a combination of a vacuum assisted closure and a wound-stimulating device. The vacuum assisted closure comprises a hydrophilic body 2 to be placed on a wound surface, a cover 4 sealing the hydrophilic body 2 and a skin portion 5A, 5B surrounding the wound surface, and a vacuum system for generating an underpressure in a closure space 6 limited by the wound surface, the skin portion 5A, 5B surrounding the wound surface and the cover 4.

The squeezable, hydrophilic body 2 can be implemented as a synthetic sponge and serves for receiving drained moisture of the wound. However, also other squeezable, hydrophilic materials can be applied for the body 2. Further, the squeezable feature of the hydrophilic body 2 causes the closure space 6 to diminish its volume during application of an underpressure. The cover 4 is formed from an airtight material in order to prevent pressure leakage in the wound-stimulating unit 1.

The wound-stimulating device comprises a connector 7 provided with an intermediate channel structure 8 having an input section 9 and multiple output sections 10, the device further comprising a pressure system for supplying wound stimulating agents to the input section 9 of the intermediate channel structure 8.

Figure 3:
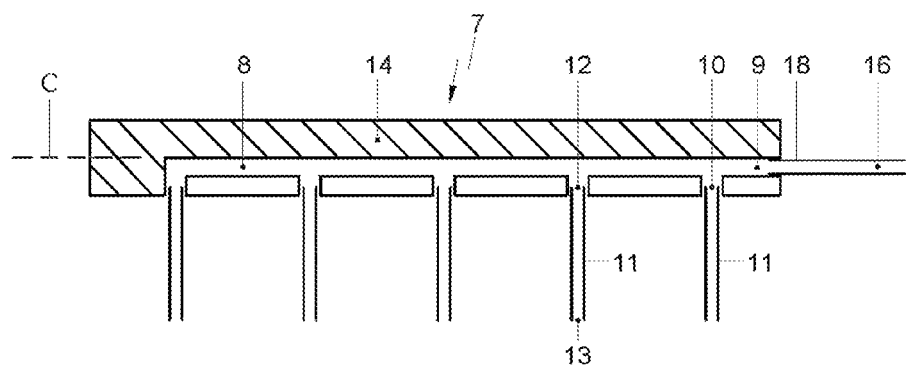
FIG. 3 shows a schematic view of a cross section of a connector of the wound-stimulating unit of FIG. 1.

FIG. 3 shows a schematic view of a cross section of a connector 7 in more detail. The intermediate channel structure 8 substantially extends in a connector plane C along the wound surface. Further, the unit 1 comprises microtubes 11 each having a connector end 12 connected to an output section of the intermediate channel structure 8, and a protruding end 13 during which wound-stimulating agents are supplied. The multiple microtubes 11 are substantially oriented transverse with respect to the connector plane C. The multiple microtubes 11 are offset with respect to each other with a distance substantially ranging from approximately 1 cm to approximately 5 cm, more preferably substantially ranging from approximately 2 cm to approximately 3 cm, depending on pathophysiological conditions of the wound. In principle, also other distances are possible, e.g. more than 5 cm. It is also possible to apply only a single microtube, e.g. if the wound surface is relatively small. Further, the multiple microtubes 11 are positioned arbitrarily or in a structured pattern, such as an array having substantially equal distances between adjacent microtubes 11. The diameter of the microtubes 11 is preferably several micrometers, e.g. ranging from circa 1 µm to 5 µM, but also other dimensions can be applied.

The intermediate channel structure 8 is formed in a rigid, solid, plate-like body 14, so that the channel structure 8 does not suffer from an underpressure applied in the closure space 6. The rigid body 14 thus forms a housing of the channel structure 8. It is of course also possible to reduce damage of the intermediate channel structure 8 by applying an open discrete framework surrounding the channel structure 8. Further, it is also possible to provide a relatively rigid lining to the channel structure.

The pressure system comprises a pressure pump 15 and a first pressure line 16 having an upstream end 17 being connected to the pressure pump 15 and a downstream end 18 that sealingly penetrates the cover 4 and is connected to the input section 9 of the intermediate channel structure 8. As the intermediate channel structure 8 is in fluid communication with the pressure pump 15 a perfusion system is obtained for supplying wound-stimulating agents, such as nutrition, growing stimulating materials and/or medicines, such as antibiotics.

As shown in FIG. 1, the connector 7 is located between a top surface 2A of the hydrophilic body 2 and the cover 4 of the vacuum assisted closure 4. The protruding ends 13 of the microtubes 11 extend away from the connector 7 and penetrate the hydrophilic body 2.

The vacuum system of the vacuum assisted closure comprises a vacuum pump 19 and a second pressure line 20 having a downstream end 21 being connected to the vacuum pump 19 and having an upstream end 22 sealingly penetrating the cover 4 and being situated in the closure space 6 limited by the wound surface, the skin portion 5A, 5B surrounding the wound surface and the cover 4. Preferably, the upstream end of the second pressure line 20 is inserted in the hydrophilic body 2.

The wound-stimulating unit 1 described above is used to treat wounds, in particular chronic wounds. In doing so, one has to perform the steps of placing the hydrophilic body 2 on the wound surface of the wound, sealing the hydrophilic body 2 and a skin portion 5A, 5B surrounding the wound surface by means of a cover 4, placing a connector 7 between a top surface 2A of the hydrophilic body 2 and the cover 4, and transferring the unit 1 from an atmospheric state wherein the pressure in the closure space 6 limited by the wound surface, the skin portion 5A, 5B surrounding the wound surface and the cover 4 is substantially at an atmospheric level to an underpressure state wherein the pressure in the closure space 6 is substantially below an atmospheric level.

Figure 2:
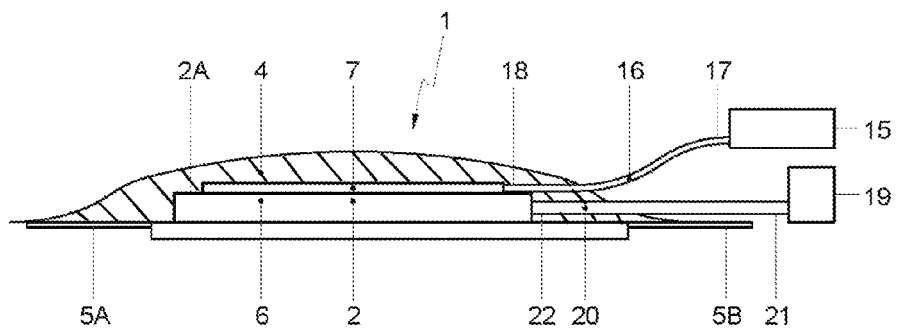
FIG. 2 shows a schematic view of a cross section of the wound-stimulating unit of FIG. 1 in a underpressure state.

By transferring the unit 1 from the atmospheric state to the underpressure state the protruding ends 13 of the microtubes 11 move from a position wherein they extend to near the wound surface, see FIG. 1, to a position wherein they penetrate through the wound surface into wound tissue below the wound surface, see FIG. 2.

Further, the pressure system of the wound-stimulating device comprises a control unit (not shown) that is arranged for supplying wound stimulating agents to the input section 9 of the intermediate channel structure 8 in a continuous or intermitted way, so that the wound-stimulating agents flow from the pressure pump 15 subsequently via the first pressure line 16, the intermediate channel structure 8 and the microtubes 11 into the wound tissue below the wound surface.

The invention is not restricted to the embodiments described herein. It will be understood that many variants are possible.

Instead of using a single hydrophilic body multiple hydrophilic bodies can be used, e.g. for reducing the chance that distinct portions of the wound contaminate each other.

Other such variants will be obvious for the person skilled in the art and are considered to lie within the scope of the invention as formulated in the following claims.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

The invention claimed is:

1. A wound-stimulating unit comprising a wound-stimulating device for use in combination with a vacuum assisted closure comprising:
    a squeezable hydrophilic body adapted to be placed on a wound surface:
    a cover sealing the hydrophilic body;
    a skin portion configured to surround a wound surface:
    a vacuum system for generating an underpressure in a closure space limited by the skin portion and the cover;
    a connector provided with an intermediate channel structure having an input section and multiple output sections;
    a pressure system configured to supply wound stimulating agents to the input section of the intermediate channel structure; and
    multiple microtubes each having a connector end being connected to an output section of the intermediate channel structure and wherein the microtubes each have a protruding end extending away from the connector and penetrating the hydrophilic body such that in an atmospheric state of the vacuum assisted closure the protruding ends of the microtubes are configured to extend to near a wound surface and that in an underpressure state of the vacuum assisted closure the squeezable hydrophilic body is configured to diminish in volume and the microtubes are configured to penetrate through the wound surface into wound tissue.

2. The wound-stimulating unit according to claim 1, wherein the intermediate channel structure is configured to substantially extend in a connector plane along a wound surface and wherein the multiple microtubes are substantially oriented transverse to the connector plane.

3. The wound-stimulating unit according to claim 1, wherein the multiple microtubes are offset with respect to each other with a distance ranging substantially from approximately 1 cm to approximately 5 cm.

4. The wound-stimulating unit according to claim 1, wherein the connector comprises a rigid, plate-like body wherein the intermediate channel structure is formed.

5. The wound-stimulating unit according to claim 1, wherein the pressure system for delivering a wound stimulating substance to the input section of the intermediate channel structure comprises a pressure pump and a first pressure line having an upstream end being connected to the pressure pump and having a downstream end for sealingly penetrating the cover and being connected to the input section of the intermediate channel structure.

6. The wound-stimulating unit according to claim 1, wherein the connector of the wound-stimulating device is located between a top surface of the hydrophilic body and the cover.

7. The wound-stimulating unit according to claim 1, wherein the vacuum system comprises a vacuum pump and a second pressure line having a downstream end being connected to the vacuum pump and having an upstream end sealingly penetrating the cover and being situated in the closure space.

8. The wound-stimulating unit according to claim 1, wherein the pressure system of the wound-stimulating device comprises a control unit that is arranged for supplying wound stimulating agents to the input section of the intermediate channel structure in a continuous or intermitted way.

9. A method for applying a wound-stimulating unit to an external wound, comprising:
    providing a wound-stimulating unit comprising:
    a squeezable hydrophilic body adapted to be placed on a wound surface:
    a cover sealing the hydrophilic body;
    a skin portion configured to surround a wound surface:
    a vacuum system for generating an underpressure in a closure space limited by the skin portion and the cover;
    a connector provided with an intermediate channel structure having an input section and multiple output sections;
    a pressure system configured to supply wound stimulating agents to the input section of the intermediate channel structure; and
    multiple microtubes each having a connector end being connected to an output section of the intermediate channel structure and wherein the microtubes each have a protruding end extending away from the connector and penetrating the hydrophilic body such that in an atmospheric state of the vacuum assisted closure the protruding ends of the microtubes are configured to extend to near a wound surface and that in an underpressure state of the vacuum assisted closure the squeezable hydrophilic body is configured to diminish in volume and the microtubes are configured to penetrate through the wound surface into wound tissue;
    placing the wound stimulating unit on the wound surface of a wound; and
    adjusting the pressure within the wound stimulating unit from an atmospheric state wherein the pressure in the closure space is substantially at an atmospheric level to an underpressure state wherein the pressure in the closure space is substantially below an atmospheric level and wherein the hydrophilic body is diminished in volume such that the microtubes penetrate the wound surface.

10. The method according to claim 9, further comprising supplying wound stimulating agents to the input section of the intermediate channel structure in a continuous or intermitted way.

* * * * *